United States Patent [19]

Sepetka et al.

[11] Patent Number: 5,551,443
[45] Date of Patent: Sep. 3, 1996

[54] GUIDEWIRE-TYPE DEVICE AXIALLY MOVEABLE BY TORQUE OR AXIAL FORCE AND METHODS FOR USE THEREOF

[75] Inventors: Ivan Sepetka, Redwood City; Phong Pham; Dai T. That, both of San Jose; Julian Nikolchev, Portola Valley, all of Calif.

[73] Assignee: Conceptus, Inc., San Carlos, Calif.

[21] Appl. No.: 379,575

[22] Filed: Jan. 21, 1995

Related U.S. Application Data

[63] Continuation of Ser. No. 83,134, Jun. 24, 1993, abandoned.

[51] Int. Cl.$^6$ ............................................. A61B 5/00
[52] U.S. Cl. ............................................. 128/772; 128/657
[58] Field of Search ............................................. 128/772, 657, 128/656; 604/93, 98, 164, 166, 170, 280, 282, 283

[56] References Cited

U.S. PATENT DOCUMENTS

| | | | |
|---|---|---|---|
| 3,906,938 | 9/1975 | Fleischacker | 128/2 M |
| 4,244,362 | 1/1981 | Anderson | 128/200 |
| 4,721,117 | 1/1988 | Mar et al. | 128/772 |
| 4,728,319 | 3/1988 | Masch | 604/22 |
| 4,763,647 | 8/1988 | Gambale | 128/657 |
| 4,798,598 | 1/1989 | Bonello et al. | 604/280 |
| 4,832,947 | 5/1989 | Sepetka et al. | 128/772 |
| 4,857,046 | 8/1989 | Stevens et al. | 604/22 |
| 4,966,163 | 10/1990 | Kraus et al. | 128/772 |
| 4,971,490 | 11/1990 | Hawkins | 128/772 |
| 5,047,040 | 9/1991 | Simpson et al. | 606/159 |
| 5,054,501 | 10/1991 | Chuttani et al. | 128/772 |
| 5,095,915 | 3/1992 | Engelson | 128/772 |
| 5,174,302 | 12/1992 | Palmer | 128/772 |
| 5,243,996 | 9/1993 | Hall | 128/772 |

*Primary Examiner*—Sam Rimell
*Attorney, Agent, or Firm*—Townsend and Townsend and Crew

[57] ABSTRACT

The present invention sets forth a guidewire-type device which can be axially moved via application of axial force and/or by application of torquing force. The device is used for accessing regions within a body. The device is used to attach to subject material within a body, and, if desired, to remove the subject material. In particular, the device and method of the invention are advantageously utilized by health care practitioners for use in accessing tortuous and difficult body areas, such as fallopian tubes.

17 Claims, 1 Drawing Sheet

GUIDEWIRE-TYPE DEVICE AXIALLY MOVEABLE BY TORQUE OR AXIAL FORCE AND METHODS FOR USE THEREOF

This application is a continuation of U.S. application 08/083,134, Jun. 24, 1993, now abandoned.

BACKGROUND OF THE INVENTION

The present invention relates to biomedical devices. More particularly, the present invention relates to a guidewire-type device for use in accessing body areas such as fallopian tubes.

Flexible wires which can be guided into and/or along passageways within a body have a number of uses in medicine. With regard to human bodies, one particular application is that the flexible wire may be introduced into a passageway such as a fallopian tube, vagina, circulatory vessel, or biliary vessel. Typically, in such applications, the flexible wire is first introduced into a catheter lumen. Thereafter, the combination of the flexible wire and the catheter are guided as a unit along a passageway toward a target site. Often, the target site is located some distance along a passageway, or is located at a site along a passageway which is only a potential space. Examples of passageways which can be potential spaces include the vagina and the fallopian tubes.

Commonly, flexible wires are advanced along a passageway only by push-pull linear motion; torquing of a guidewire is used to orient the wire, particularly for wires which have an angled distal tip. Unfortunately, due to the minute dimensions and delicacy of the passageways that are involved in biomedical procedures, movement of traditional guidewires by push-pull force only is sometimes insufficient to advance the wire, especially when it becomes located at a tortuous site, and encounters difficulty passing through this site.

Heretofore, guidewires have utilized small diameter coils at their distal-most tip. In the construction of distal coils for guidewires of this type, the coils are typically constructed of narrow diameter wire coiled in a tightly spaced configuration. Such coils have been utilized to maintain flexibility of the guidewire at the distal tip, while attempting to avoid a physical structure which could puncture the tissues of the channel through which the guidewire is passing. Again, these wires could only be advanced using a push-pull motion.

In difficult situations, such as blocked or tortuous passage (as exemplified by fallopian tubes), typical guidewires cannot be advanced using push-pull force. This limitation could lead to surgery or other expensive interventions to treat or access these body areas. Thus, alternative devices and methods are needed to provide access to these sites.

SUMMARY OF THE INVENTION

The present invention sets forth a guidewire-type device which overcomes problems present in the prior art for accessing areas in bodies. Advantageously, the device and method of the invention are readily utilized by health care practitioners. In particular, the device overcomes problems in tortuous and/or difficult to access areas, such as fallopian tubes.

Accordingly, an elongate guidewire-type device is set forth that comprises a proximal section and a distal section. The distal section comprises a core and a protruding area which is attached to the core. The protruding area can be attached by means such as soldering or by a biocompatible adhesive. The protruding area has a spiral configuration and delimits a spirally encircling recession. The protrusion has turns as it spirals along the distal section of the device. At any spot along the device, the protrusion has an axial length when measured along an axis substantially parallel to the longitudinal axis of the device. Additionally, each turn is substantially equally spaced, with respect to each successive turn, in other words, the turns have uniform pitch spacing between them when measured along an axis substantially parallel to the longitudinal axis of the elongate guidewire-type device. The pitch spacing between turns is greater than the axial length of a protrusion turn.

Alternatively, a device, in accordance with the invention, having physical shape in accordance with that just described, is constructed substantially entirely of polymeric materials, and may be of a single piece. Furthermore, due to the construction of the device, the length of the device is constant during its use. In other words, it is substantially incompressible in its cross-sectional aspect which would cause axial lengthening or shortening of the device during use.

Thus, a device in accordance with the invention is used to access sites within a body. It is especially useful for accessing fallopian tubes. It is also used to attach to a subject material or object in a body; in one embodiment, once it has attached to material or object in a body, it is used to remove the subject material or object.

Advantageously, a device in accordance with the invention can move axially in a body by application of axial force or by application of torque force.

DETAILED DESCRIPTION OF THE INVENTION

Figure 1:
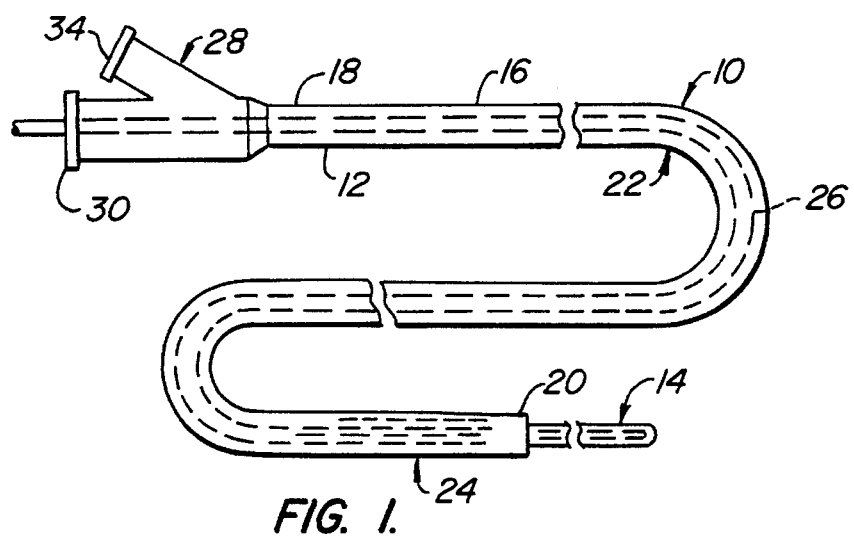
FIG. 1 shows a catheter apparatus, comprising a guidewire-type device constructed in accordance to the present invention.

FIG. 1 depicts a catheter device apparatus 10 for use in accessing an internal site in a body, preferably along a passageway. The device generally comprises a catheter 12 and a guidewire-type device 14 constructed according to the present invention, as set forth herein. Guidewire-type devices may be constructed from metals, polymers, or both materials, as well described in more detail hereinafter.

Referring again to FIG. 1, it is seen that the catheter apparatus comprises an elongate tubular member 16 having proximal and distal ends 18, and 20, respectively. The tubular member is preferably about 40–300 cm in length, typically between about 60–70 cm in length. Tubular member 16 is preferably composed of a relatively stiff proximal section 22, which extends along a major portion of the catheter length, and one, or more, relatively flexible distal sections, such as indicated by section 24. Relatively flexible distal sections, such as section 24, provide the catheter with increased ability to track guidewire-type device 14 through bends and turns which are encountered as the catheter is moved in a body. An inner lumen 26, indicated by dashed lines, extends between the proximal and distal ends of the catheter.

The catheter apparatus advantageously comprises an end fitting 28 through which guidewire-type device 14 is received, and through which fluid material can be introduced into the catheter lumen. One suitable standard fitting is illustrated in FIG. 1, and has an axially extending port 30 through which the guidewire-type device is received, and thus can be rotated (torqued) and advanced or retracted axially within catheter 12, during a catheter and/or guidewire placement procedure. An external port 34 can also be used, which allows for delivery of fluid material through the catheter around the guidewire or into inner lumen 26, after closing-off of port 30.

Figure 2:
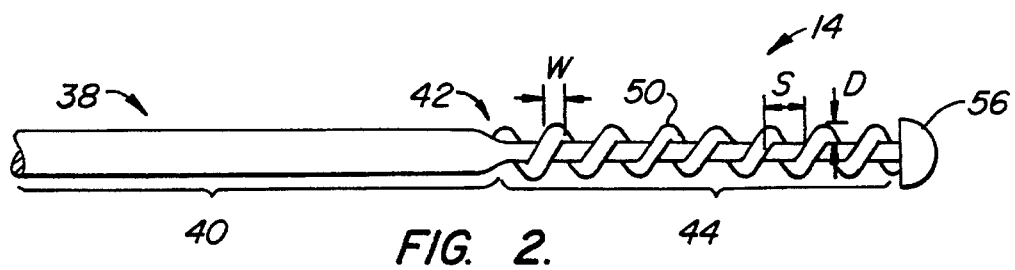
FIG. 2 depicts an enlarged distal-end portion of an embodiment of a device constructed in accordance with the present invention.

FIG. 2 shows an enlarged view of a distal end section of an embodiment of guidewire-type device 14. As depicted in FIG. 2, the device comprises an elongate wire core 38. In a presently preferred embodiment, wire core 38 is formed of a flexible, torqueable wire filament material, such as stainless steel, and has a total length typically between 50–300 cm. In the embodiment illustrated in FIG. 2, wire core 38 comprises, moving from a proximal to a distal direction, a proximal section 40 (which is truncated at the left end of FIG. 2), a tapered region 42, and a distal section 44. The distal section 44 will preferably itself be tapered in the distal direction, either gradually or in two or more sections. Proximal section 40 preferably has a substantially uniform diameter of between about 2–30 mils (thousandths of an inch) along its length. The distal section 44 of the wire core 38 extends over 5–30 cm, preferably about 20 cm, of the wire core and preferably has a diameter of about 2–30 mils, optionally being tapered to a reduced diameter in the distal direction The distal section 44 of the wire core 38 is helically encircled by a coil 50. The coil substantially extends from tapered segment 42 to the distal-most end of the guidewire. As depicted in FIG. 2, a distal cap 56 secures coil 50 to the wire core 38. A preferred manner of producing the cap 56 is by soldering. The coil 50, however, can be attached in accordance with other procedures, as will be appreciated by those of ordinary skill in the art. Preferably, a second attachment point is located at the proximal end of coil 50. Additional attachment points can be located along the axial extent of coil 50. Additional attachment points serve to prevent axial compression, torsion, or unwinding, of coil 50 as it is being moved through a body. It is advantageous that the outer diameter of coil 50 corresponds to the outer diameter of the proximal section 40 of wire core 38 to avoid undue friction or disadvantageous impingement with surrounding matter. This construction is especially advantageous as it allows a device in accordance with the invention to move smoothly through regions of the body that other guidewires or biomedical devices could not pass through.

Typically, coil 50 is constructed of material such as stainless steel, platinum, platinum alloys, or a combination of stainless steel and platinum. As is appreciated by one of ordinary skill in the art, the coil 50 can have a cross-sectional shape that is rounded, or other shapes such as flattened, as with a ribbon-type material. Also, some adhesive or filler may be used to smooth the transition between the distal tip and the rest of the device. As is readily appreciated by those of ordinary skill in the art, a material which provides radio capacity, such as platinum or a platinum alloy is advantageously used in the tip.

Two parameters are relevant to the construction of a device of the present invention which axially moves through a body by application of axial force, by application of torque force, or by a combination of such forces. The first parameter relates to the axial spacings between successive turns in the coil or coil-like structure at or near the distal end of the guidewire. The second parameter relates to the depth of the recession between successive turns of the coil 50.

For enhanced ability to axially advance the guidewire 14 through a body lumen, it is necessary that the spacings 5 be greater than the width W of successive turns in the coil. For example, for an embodiment for use in moving guidewire-type device 14 through tissues such as a fallopian tube, coil spacings S are preferably between 0.003 inches and 0.1 inches, and most preferably between 0.01 and 0.02 inches. The depth D of the recession between adjacent turns is between 0.0005 and 0.020 inches, and more preferably between 0.003 and 0.013 inches.

Figure 3:
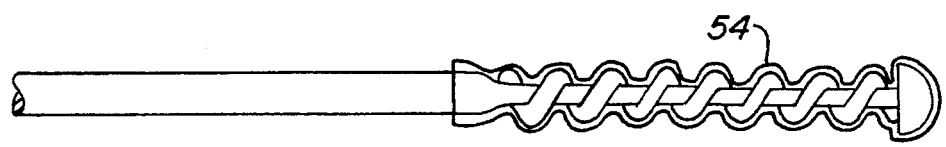
FIG. 3 illustrates an enlarged distal-end portion of an alternate embodiment of a device constructed in accordance with the present invention having a polymeric sleeve at its distal end.

It is advantageous to encase coil 50 in a sleeve 54, as illustrated in FIG. 3. Preferably, sleeve 54 is a lubricous sleeve. Prior to the present invention, it was believed that encasing the distal end of the device in a lubricous material would prevent the guidewire-type device from axially moving upon application of a torque force. Advantageously, however, it was discovered that axial movement upon application of torque force to a device in accordance with the invention was still accomplished, and that axial movement was actually facilitated. Furthermore, it was found that here was less possibility of causing any tissue damage and, as a particular advantage, it was found that encasing the distal end of the device in a lubricous sleeve facilitated movement of the guidewire-type device through passageways which previously were not traversable. Also, as noted above, some adhesive or filler may be used to smooth the transition between the distal tip and the rest of the device.

As noted above, it is preferable that the region of the wire core encompassed by coil 50 is also encompassed in an elongate polymeric sleeve 54. The length of the sleeve is preferably about 5–30 cm, corresponding to the length of the coil, and the wall thickness of the sleeve is preferably about 1–10 mils. As noted, it is preferred that the material comprising sleeve 54 is lubricous. Preferred polymers comprise Teflon™, a high-density polyolefin (e.g., polyethylene), or polyurethane. Polymeric sleeve 54 is advantageously bonded, or otherwise tightly affixed to the core wire. Most preferably, sleeve 54 is affixed to the distal end of the device by means of heat induced shrinkage. Other suitable coatings comprise polymers having exposed hydrogens, such as polyester, polycarbonate, polyvinylchloride, latex or silicone rubber, polystyrene, and a surface coating formed of highly hydrophilic, low-friction polymer, such as polyvinylpyrrolidone, polyethyleneoxide, polyhydroxyethylmethacrylate, or copolymers thereof; these coatings are applied in accordance with methodologies known to those of ordinary skill in the art.

Alternatively, sleeve 54 is formed by other conventional methods, such as by extrusion, molding, or dip coating. In the situation where the sleeve is formed by extrusion, the extruded sleeve can be attached to the wire core by friction fit, adhesive, or, most preferably, heat-shrinkage. In the case of a molded sleeve, a polymer material is preferably molded directly on the distal region of the wire core. The sleeve-encased portion of the wire may be surface-roughened, such as by chemical treatment, prior to molding. Forming the sleeve by dip coating is accomplished by successive dipping of the distal region of the device in a suitable polymer solution, in accordance with conventional methods of polymer coat application.

Figure 4:
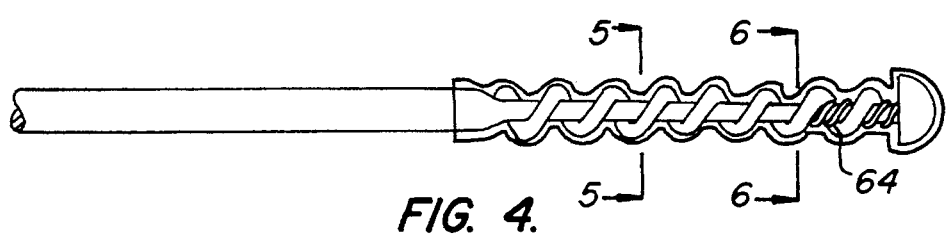
FIG. 4 illustrates an enlarged distal-end portion of an alternate embodiment of a guidewire-type device constructed in accordance with the present invention having a polymeric sleeve at its distal end, and a centering coil.
Figure 5:
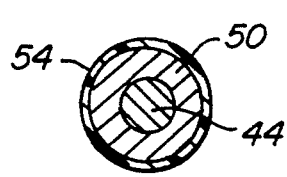
FIG. 5 illustrates an cross-section of the embodiment of FIG. 4 taken along plane 5—5.
Figure 6:
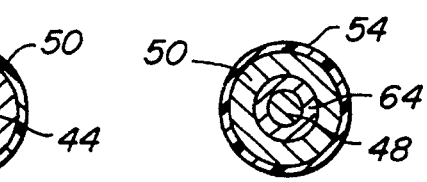
FIG. 6 illustrates an cross-section of the embodiment of FIG. 4 taken along plane 6—6.

An alternate embodiment of the device is illustrated in FIG. 4. As illustrated in FIG. 4, a centering coil 64 is illustrated near the distal end of guidewire-type device 14 which has a distally tapered wire core 38. Centering coil 64 is coaxially encompassed by coil 50. Advantageously, centering coil 64 serves to more securely affix coil 50 to the wire core, as reflected by the cross-sectional illustration 30 of FIG. 6. Typically, coil 64 is between 2 mm to 6 cm in length, most preferably 1 cm. FIG. 6 depicts a cross-section taken along plane 6—6 in FIG. 4; FIG. 5 depicts a cross-section taken along the plane 5—5 in FIG. 4. As illustrated in FIG. 5, core wire section 44 substantially fills the inner diameter defined between spirals of coil 50. However, as illustrated in FIG. 6, centering coil 64 substantially fills the space defined between the more narrowed distal segment 48 of the wire core, and between the surface defined by the inner aspect of outer coil 50. Thus, placement of centering coil 64, in accordance with securing methodologies known to those of skill in the art, results in a more secure and uniform orientation of coil 50. Coil 64 is typically affixed with solder or biocompatible adhesive.

In additional alternate embodiment of the guidewire-type device of the present invention (not illustrated), a biomedical device which is axially moved by application of axial force and/or by application of torsional force is constructed substantially of polymeric materials. This substantial polymeric embodiment is preferably constructed of a single piece of polymeric material. Such construction is carried out in accordance with methodologies known in the industry for constructing biomedical devices, more particularly, guidewire-type devices, of polymeric materials, such as polypropylene, polyethylene, or Teflon®.

For the embodiment of guidewire-type device 14 substantially constructed of polymeric materials, the outer surfaces of the device correspond to the dimensional parameters set forth herein. For example, the outer surfaces of a substantially polymeric device of the invention can correspond to the outer surfaces of an embodiment such as illustrated in FIG. 1. Alternatively, it can also be advantageous for a substantially polymeric guidewire-type device formed of polymeric materials to have the distal end encompassed in a separate polymeric sleeve 54, the fundamental dimensional parameters for a sleeve-encased guidewire-type device as set forth herein are applicable. Thus, the substantially polymeric device has an elongate proximal section and a distal section; wherein the distal section has a recessed area and a protruding raised area. Accordingly, the raised area forms a spirally encircling protrusion and the protrusion delimits a spirally encircling recession. Alternatively, for guidewire-type device substantially formed of polymeric materials for which it is advantageous to encompass the distal end in a polymeric sleeve, the dimensional parameters for a sleeve-encased guidewire-type device as set forth herein are applicable. Advantageously, when a substantially entirely polymeric guidewire-type device in accordance with the present invention is constructed with a sleeve, such as described herein, this allows the device to be moved through body passageways that are exceedingly difficult to traverse.

Another way to achieve a device in accordance with the invention having a function of advancing by torque is by removing materials, thereby creating spiral-type helical recessions and corresponding protrusions.

In one particular application of a device in accordance with the present invention, the device is used to attach to subject material within a body. For example, the device is introduced into a mammalian body, such as into a circulatory vessel, and then is advanced via application of axial or torquing force. The device is advanced into the subject material. Advantageously, the present invention allows the device to enter the material via application of either axial or torquing force. Thereafter, the material is removed from the body by retracting the device. Examples of materials that can be attached to the device and then removed comprise thrombus material, atherosclerotic material, or foreign materials that are within the circulatory system, such as coils. Alternatively, the device may be advanced through the vagina, uterus and into a fallopian tube to attach to and then remove material that had been placed in the fallopian tube to achieve fallopian tube blockage.

It must be noted that as used herein and in the appended claims, the singular forms "a," "and," and "the" include plural referents unless the context clearly dictates otherwise. Thus, for example, reference to "a formulation" includes mixtures of different formulations and reference to "a method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the presently preferred methods and materials are now described. All publications mentioned herein are incorporated herein by reference to describe and disclose specific information for which the reference was cited in connection with. All examples herein are provided for the purposes of illustration and clarification. It is understood that the invention is limited solely by the following claims.

What is claimed is:

1. A guidewire-type device comprising:

a core having an elongate proximal section and an elongate distal section; and a helical element disposed over the distal section, wherein successive turns of the helical element have a uniform pitch and are spaced-apart by a distance which is greater than the width of the helical element;

wherein the core wire substantially fills an inner diameter defined by the helical element, and wherein the helical element is attached to the core at a distal end of the helical element and at a plurality of attachment points along the distal section.

2. A guidewire-type device as in claim 1, wherein the turns are spaced-apart by a distance in the range from 0.003 inches to 0.1 inches.

3. A guidewire-type device as in claim 1, wherein the elongate distal section of the core has a smaller diameter than the proximal section.

4. A guidewire-type device as in claim 3, wherein the helical element has an outside diameter which is substantially equal to that of the proximal section of the core.

5. A guidewire-type device as in claim 1, wherein a recession having a depth of from 0.0005 inches and 0.020 inches is disposed between successive turns of the coil.

6. A guidewire-type device as in claim 1, wherein the distal section has a length in the range from 5 cm to 300 cm.

7. A guidewire-type device as in claim 1, wherein the helical element is a helical coil which is attached continuously along the distal section of the core.

8. A guidewire-type device as in claim 1, wherein the helical element is formed as a unitary polymeric structure with the core.

9. A guidewire-type device as in claim 1, further comprising a polymeric sleeve disposed over the helical element and the core, wherein the polymeric sleeve contacts the core between the turns of the helical element so that an outer surface of the polymeric sleeve defines a recession between the successive turns of the helical element.

10. A guidewire-type device as in claim 1, further comprising a centering coil coaxially aligned inside the helical element over a decreased diameter distal segment of the core adjacent to the distal end of the distal section, so that the centering coil substantially fills a space between the inner diameter defined by the helical element and the distal segment.

11. A method for advancing a guidewire through a body lumen, said method comprising:

proveding a guidewire comprising a core having an elongate proximal section and an elongate distal section, a helical element disposed over the distal section and having successive turns which are spaced-apart by a distance greater than the width of the helical element;

introducing the elongate distal section of the guidewire into a body lumen;

engaging the helical element against the luminal walls; and rotating the core while the helical element is engaged against the luminal walls so that the helical element axially advances the guidewire.

12. A method as in claim 11, further comprising applying axial force to the proximal section to advance the guidewire.

13. A method as in claim 11, wherein the helical element advances the guidewire without substantially applying axial force to the proximal section.

14. A method as in claim 11, wherein the distal section of the guidewire is advanced within a fallopian tube.

15. A method as in claim 11, wherein the distal section of the guidewire is straight, so that the rotating step does not steer the guidewire.

16. A method for advancing a guidewire within a fallopian tube, said method comprising:

introducing a distal section of the guidewire into the fallopian tube;

engaging a helical element of the distal section of the guidewire against a tubal wall of the fallopian tube; and rotating a proximal section of the guidewire while the helical element is engaged against the tubal wall so that the distal section axially advances the guidewire.

17. A guidewire-type device comprising:

a core having an elongate proximal section and an elongate distal section;

a helical element disposed over the distal section, wherein each successive turn of the helical element is spaced-apart by a distance which is greater than the width of the helical element;

a polymeric sleeve encasing distal portions of the helical element and the core so that an outer surface of the polymeric sleeve defines a recession between the successive turns of the helical element;

wherein the core wire substantially fills an inner diameter defined by the helical element.

* * * * *